United States Patent [19]

Chu et al.

[11] Patent Number: 5,278,167
[45] Date of Patent: Jan. 11, 1994

[54] 6-PYRIDYL SUBSTITUTED PYRIMIDINE DERIVATIVES

[75] Inventors: Shih H. Chu, Barrington, R.I.; Yung C. Cheng, Woodbridge, Conn.; Bai C. Pan, Providence, R.I.

[73] Assignee: Brown University Research Foundation, Providence, R.I.

[21] Appl. No.: 882,584

[22] Filed: May 13, 1992

[51] Int. Cl.$^5$ .................. A61K 31/505; C07D 401/12
[52] U.S. Cl. .................................. 514/269; 514/270; 544/300; 544/310; 544/360; 544/363; 544/364
[58] Field of Search ............... 544/360, 364, 310, 363; 514/269, 270; A61K 31/505

[56] References Cited

U.S. PATENT DOCUMENTS

| | | | |
|---|---|---|---|
| 3,282,921 | 11/1966 | Verheyden et al. | 536/23 |
| 3,755,295 | 8/1973 | Verheyden et al. | 536/23 |
| 3,775,397 | 11/1973 | Etzold et al. | 536/23 |
| 3,817,982 | 7/1974 | Verheyden et al. | 536/23 |
| 4,071,680 | 1/1978 | Cook | 536/23 |
| 4,093,715 | 6/1978 | Liu et al. | 536/23 |
| 4,128,639 | 12/1978 | Liu et al. | 514/50 |
| 4,210,638 | 7/1980 | Greer | 536/23 |
| 4,230,698 | 10/1980 | Bobek et al. | 536/23 |
| 4,331,662 | 5/1982 | Eckstein et al. | 536/23 |
| 4,604,382 | 8/1986 | Liu et al. | 514/49 |
| 4,681,933 | 7/1987 | Chu et al. | 536/23 |

OTHER PUBLICATIONS

Horwitz, J. Org. Chem. vol. 29, pp. 2076–2078 (1964).
Liu et al, J. Med. Chem. pp. 109–112 (1978).
Liu et al, Biochem. Pharmacol. vol. 36, pp. 311–316 (1987).

*Primary Examiner*—Cecilia Tsang
*Attorney, Agent, or Firm*—Thomas J. Engellenner; Matthew P. Vincent

[57] ABSTRACT

Novel 6-pyridyl substituted pyrimidine derivatives are disclosed for use as antiviral agents, particularly for the treatment of retroviral infections such as HIV infections and related disorders, as well as for use in anti-cancer therapies to improve the efficacy of anti-cancer therapeutics. These compounds and their pharmacologically acceptable salts operate to disrupt viral replication an exhibit lower cell toxicity, thereby providing more efficient agents for use alone or in conjunction with other chemical or biological agents to provide prolonged antiviral therapy. In addition, the compounds can be used to increase the efficacy of anti-cancer therapeutics including 5-fluropyrimidines such as 5-fluorouracil, thereby reducing the dosage requirement of the therapeutic in anti-cancer therapies so as to decrease toxic effects to the host.

13 Claims, 1 Drawing Sheet

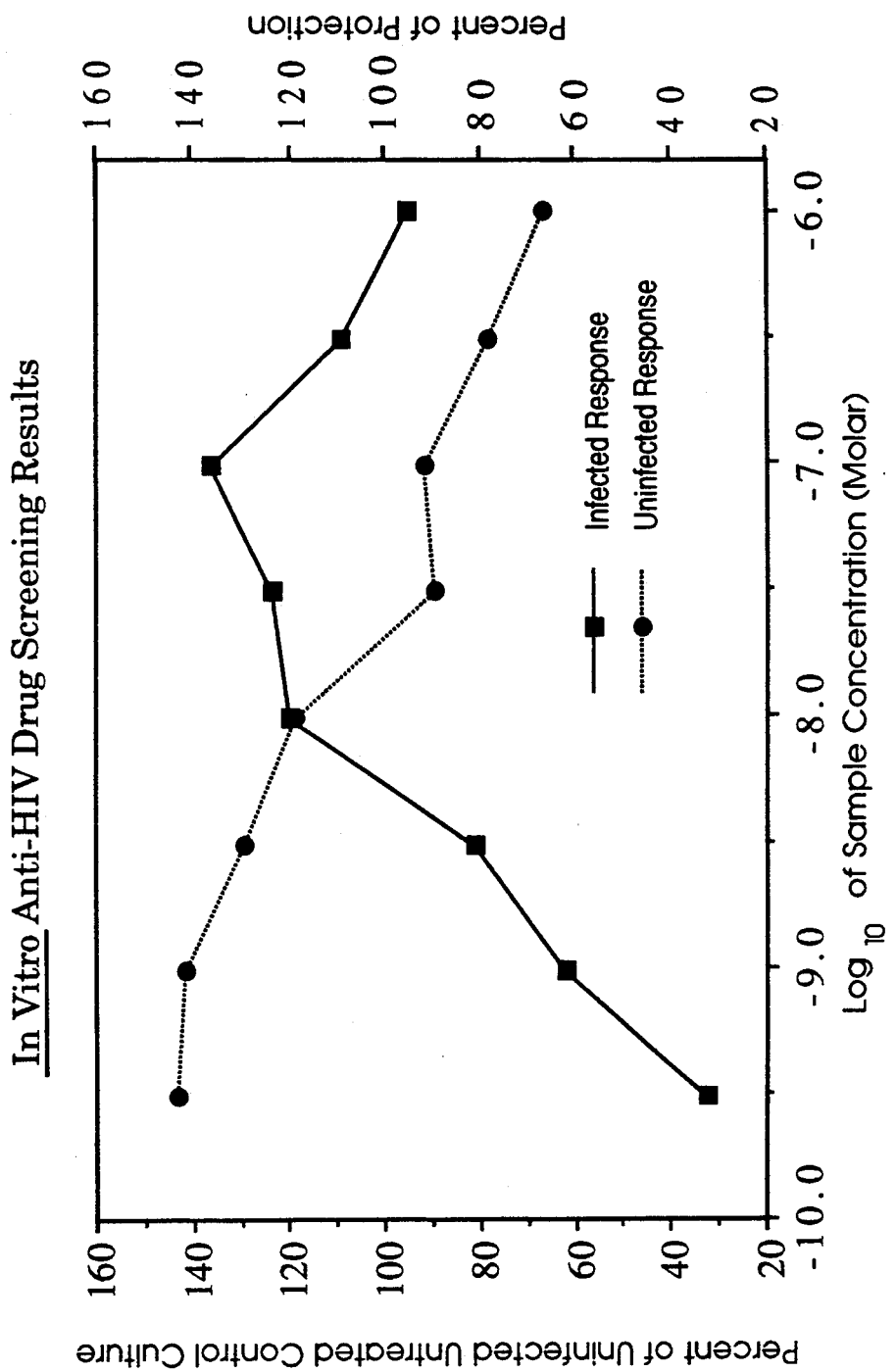

6-PYRIDYL SUBSTITUTED PYRIMIDINE DERIVATIVES

The U.S. Government has rights in this invention pursuant to CA 39427 and CA 44358, awarded by the National Institute of Health.

BACKGROUND OF THE INVENTION

The present invention relates to synthesis and pharmaceutical compositions of novel 6-pyridylthio- and 6-pyridylseleno-substituted pyrimidine derivatives, useful for the treatment of infectious viral diseases, and for improving the efficacy of of anti-cancer therapeutics such as 5-fluorouracil in cancer therapy. With particular regard to antiviral activity, the compounds of this invention are useful in the treatment of Acquired Immunodeficiency Syndrome (AIDS) and related illnesses.

Acquired Immunodeficiency Syndrome is generally accepted to be the result of infection with a type of retrovirus termed the Human Immunodeficiency Virus (HIV). A number of strains or classes of HIVs have been identified, and it appears that HIVs are part of a broader family of retroviruses having similar genomes that are responsible for a wide range of diseases having diverse clinical manifestations.

In cases of AIDS, the infections are characterized by a marked depression in the hematological profile of the host and a general loss of the host immune response to invading pathogens, leaving the afflicted individuals extremely vulnerable to opportunistic infections by other microbes. In early stages of the infection, a number of less life-threatening manifestations have been reported and are generally referred to as AIDS-related complex.

At present, management of patients with HIV infections typically involves the administration of a pyrimidine nucleoside, such as, for example, azidothymidine (3'-azido-2',3'-deoxythymidine or "AZT"). Such chemotherapeutic agents function by inhibiting the reverse transcriptase of the HIV and reducing the cytopathic effects of the virus.

For further disclosures of pyrimidine nucleosides having antiviral properties and methods of synthesizing such compounds, see U.S. Pat. No. 3,282,921 issued to Verheyden et al. on Nov. 1, 1966; U.S. Pat. No. 3,687,931 issued to Verheyden et al. on Aug. 29, 1972; U.S. Pat. No. 3,755,295 issued to Verheyden et al. on Aug. 28, 1973; U.S. Pat. No. 3,775,397 issued to Etzold et al. on Nov. 27, 1973; U.S. Pat. No. 3,817,982 issued to Verheyden et al. on Jun. 18, 1974; U.S. Pat. No. 4,071,680 issued to Cook on Jan. 31, 1978; U.S. Pat. No. 4,093,715 issued to Lin et al. on Jun. 6, 1978; U.S. Pat. No. 4,128,639 issued to Lin et al. on Dec. 5, 1978; U.S. Pat. No. 4,210,638 issued to Greer on Jul. 1, 1980; U.S. Pat. No. 4,230,698 issued to Bobek et al. on Oct. 28, 1980; U.S. Pat. No. 4,331,662 issued to Eckstein et al. on May 25, 1982; U.S. Pat. No. 4,604,382 issued to Lin et al. on Aug. 5, 1986; U.S. Pat. No. 4,681,933 issued to Chu et al. on Jul. 1, 1987; Horwitz, Vol. 29, *J. Org. Chem.*, pp. 2076-2078 (1964); Lin et al., Vol. 21, *J. Med. Chem.*, pp. 109-112 (1978); Lin et al., Vol. 36, *Biochem. Pharmacol.*, pp. 311-316 (1987); and Schinazi et al., Interscience Conference on *Antimicrobial Agents and Chemotherapy*, Abstract #369 (1987), herein incorporated by reference.

To date no compounds for the chemotherapy of AIDS have been discovered that are completely satisfactory or even as effective as AZT. Only a few others (3'-azido-2',3'-dideoxycytidine, 2',3'-dideoxyinosine, etc.) have even reached clinical trials. In view of the epidemic spread of the disease, there is a pressing need to find compounds that will be active against HIV during the latent stage of its life cycle to facilitate complete abrogation of the virus.

The treatment of AIDS with AZT has a number of drawbacks. In the first place it is only active against the HIV virus during the part of its life cycle during which it is replicating itself. AZT does not eradicate the virus as long as it remains latent, it only slows down the progress of the disease. It must be taken daily for an indefinite period of time, perhaps years, to keep the virus more or less in check. AZT is a toxic drug. In many cases, over a long period of time AZT causes damage to bone marrow and the hematopoietic system, and may give rise to neurological disorders. It would therefor be desirable to have other drugs available which are at least as good as AZT, which could be varied to avoid long-term side effects, and that would be more effective and less toxic.

In the field of cancer chemotherapy, the use of halogenated pyrimidine bases such as 5-fluorouracil (5-FUra), and halogenated pyrimidine nucleosides such as 5-fluoro-2'-deoxyuridine (5-FdUrd) as chemotherapeutic agents is well documented in the art (Heidelberger, C., in *Antineoplastic and Immune Suppressive Agents* Part II, A. C. Sartorelli and D. G. Jones ed.s, pp. 193-231, (Springer-Verlag, Heidelberg, 1975)). However the halogenated pyrimidine nucleosides are rapidly degraded to their respective pyrimidine bases, thereby reducing their effectiveness against the cancer tissue they are meant to treat. Moreover, cytotoxicity is caused by 5-FUra's toxic metabolites that are produced by the catabolism process.

These factors have limited the use of 5-FUra due to a low therapeutic index, leading to studies aimed at increasing its antitumor activity and decreasing its toxic effects on host tissue by combining 5-Fura with agents such as methotrexate (Cadman et al. (1979) *Science* 205:1135), N-(phosphonacetyl)-L-aspartate (Martin et al. (1989) *Cancer* 45:1117) allopurinol (Schwartz et al. (1980) *Cancer Res.* 40:1885), 5-benzylacyclouridine and AZT. Susceptible normal tissue can also be selectively rescued by the subsequent administration of large doses of uridine (Klubes et al. (1983) *Cancer Res.* 43:3182). However, this augmentative therapy is hampered by toxicity associated with the administration of high uridine dose, such as phlebitis and pyrogenic reactions.

It is a goal of this invention to provide a compound which is an effective antiviral agent, particularly against the retrovirus HIV.

It is another goal of this invention to provide an antiviral agent which is less toxic to a subject than AZT.

It is a further goal of the invention to increase the efficacy of 5-fluorouracil treatment in cancer therapy while decreasing host toxicity due to 5-fluorouracil and its metabolites.

SUMMARY OF THE INVENTION

Novel 6-pyridyl substituted pyrimidine derivatives are disclosed for use as antiviral agents, particularly for the treatment of retroviral infections, such as HIV infections and related disorders. These compounds and their pharmacologically acceptable salts operate to disrupt viral replication. As a result of their pyridyl-substituted nature, these compounds exhibit a greater water solubility than analogous phenyl-substituted pyrimidine derivatives.

The term "6-pyridyl-substituted" as used herein refers to compounds having a group containing at least one pyridyl moiety linked to a pyrimidine derivative at the 6-position carbon atom of the pyrimidine ring, via a sulfer or selenium atom. Such 6-pyridyl-substitutions include, for example, pyridylthio and pyridylseleno moieties, and derivatives thereof.

The term pyrimidine derivatives refer to 2,4-pyrimidinedione analogues comprising further substitutions at the 1, 5 and 6 position of the pyrimidine ring.

The compounds of the present invention can be represented by the following general formula:

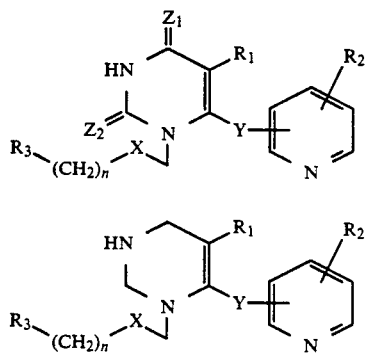

wherein $R_1$ is selected from the group consisting of a hydrogen, a halogen, an alkyl, an alkenyl, an alkynyl, a trifluoromethyl, a phenylthio, and a idylthio; $R_2$ is selected from the group consisting of a hydrogen, a halogen, an alkyl, an amino, a mono- or di-substituted amino, an azido alkyl, an amino alkyl, and a mono- or di-substituted amino alkyl; $R_3$ is selected from the group consisting of a hydrogen, a halogen, an alkyl, an aryl, a substituted aryl, an azido alkyl, an amino alkyl, a mono- or di-substituted amino alkyl, a trifluoromethyl, a pyridyl, and a quinolyl; X is selected from a group consisting of sulfur and oxygen; Y is selected from a group consisting of sulfur and selenium; N is in the range of 0 to 5; and $Z_1$ and $Z_2$ are each selected from a group consisting of oxygen, sulphur and selenium.

The compounds of the present invention are particularly advantageous insofar as they possess antiviral activity and they do not appear to adversely affect normal cell growth. Because the compounds of the present invention are water soluble, they can be administered intravenously in physiological saline solution (e.g., buffered to a pH of about 7.2 to 7.5). Conventional buffers, such as triphosphates, bicarbonates or citrates can be used for this purpose. The compounds can also be administered orally as pharmacologically acceptable salts.

In addition, cytotoxicity studies show that the combination of 5-fluoropyrimidine analogs and a 6-pyridyl substituted pyrimidine derivative of this invention is more effective against human cancer cells than the 5-fluoropyrimidine alone. Thus, the compounds of the present invention appear to be excellent potentiators of certain anti-cancer therapeutics, including 5-fluoropyrimidines such as 5-FUra, in cancer chemotherapies.

BRIEF DESCRIPTION OF THE DRAWINGS

FIG. 1 is a graphical representation of the anti-HIV activity of 1-benzyloxymethyl-5-ethyl-6-(α-pyridylthio) uracil.

DETAILED DESCRIPTION OF THE INVENTION

Specific compounds of this invention include the following:
1-benzyloxymethyl-5-ethyl-6-(α-pyridylthio) uracil
1-benzyloxymethyl-5-ethyl-6-(α-pyridylseleno) uracil The molecular structures of these exemplary 6-pyridyl-substituted pyrimidine derivatives are shown below:

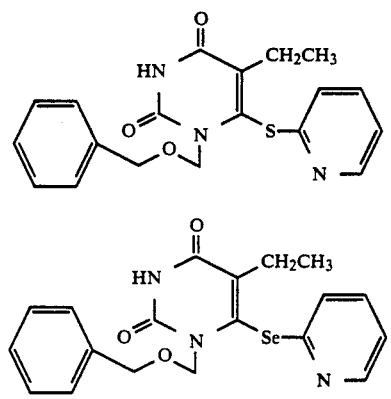

The active materials of the present invention can be employed in dosages and amounts which are conventional in the art. Thus, the materials can be used in humans at dosages ranging from about 1 mg/kg to about 200 mg/kg total body weight per day. The dosages may be administered at once or may be divided into a number of smaller doses to be administered at varying intervals of time.

The dosage regimen of combination therapy may be adjusted to provide the optimum therapeutic response. For example, the most preferred dosage will vary with the particular agent chosen and, during administration, the dose may be proportionally increased or reduced as indicated by the exigencies of the therapeutic situation. A decided practical advantage is that the active compounds may be administered in any convenient manner, such as by the oral, intravenous, intramuscular, or subcutaneous routes.

The active compounds may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compounds may be incorporated with excipients and used in the form of ingestible tablets, buccal tablets, troches, capsules, elixirs, suspensions syrups, wafers, and the like.

Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compounds sucrose as a sweetening agent, methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparations and formulations.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile, injectable solutions or dispersions. In all cases, the form must be sterile and must be fluid to the extent that easy syringability exists. It must be stable under the conditions of manufacture and storage and must be preserved against the contaminating action of microorganisms, such as bacterial and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monosterate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The invention will next be described in connection with certain non-limiting, specific examples which are included herein for purposes of illustration. It should be clear that the examples provide general schemes which outline the basic methods for synthesizing some of the compounds of the present invention. Unless otherwise specified, the 6-pyridyl-substitutions described below encompass a generic class including, for example, 6-pyridylthio and 6-pyridylseleno substituted pyrimidine derivatives.

EXAMPLE 1

1-benzyloxymethyl-5-ethyl-6-($\alpha$-pyridylthio) uracil

In one embodiment, 1-benzyloxymethyl-5-ethyl-6-($\alpha$-pyridylthio) uracil according to the present invention can be prepared from 5-ethyl-1-benzyloxymethyl uracil, according to the following synthesis routes:

2,4-bis-o-(trimethylsilyl)-5-ethyl uracil was made from a mixture of 5.6 g 5-ethyl uracil (Niedzwicki et al. (1982) *Biochem Pharm.* 31:1857, incorporated by reference herein) and 152 mg ammonium sulfate in 20 ul of hexamethyl disalazane by heating at reflux under an inert atmosphere until the 5-ethyl uracil has dissolved. After removal of excess hexamethyl disalazane under reduced pressure, the residue was distilled in vacuo to give 2,4-bis-o-(trimethylsilyl)-5-ethyl uracil.

The synthesis of 5-ethyl-1-benzyloxymethyl uracil is carried out by mixing 2.16 g benzyl alcohol and 1.2 g of paraformaldehyde in 20 ml of dry HCl gas in methylene chloride. The suspension was cooled to 0° C. overnight, washed with water and dried over anhydrous magnesium sulfate.

The filtered solution of the chloromethylated product in methylene chloride was then added to a suspension of 5.08 g 2,4-bis-o-(trimethylsilyl)-5-ethyl uracil and 4.1 g powdered potassium carbonate in 20 ml of methylene chloride and stirred at room temperature for 24 hours.

The reaction mixture was then cooled to 0° C. and 10 ml water was added to dropwise. The solution was filtered to give crystals. Concentration of methylene chloride under reduced pressure gave another portion of product. The two product fractions were combined and recrystallized from ethanol.

5-ethyl-1-benzyloxymethyl uracil (520.5 mg, 2 moles) was dissolved in 10 ml of dry Tetrahydrofuran (THF) and cooled to −78° C. To the solution was added 3.6 ml of 1.4M Lithium Diisopropylamide (LDA) dropwise while stirring. After addition, the solution was stirred at −78° C. for 1 hour and 1.1 g (5 moles) of dipyridyl disulfide in 3 ml of dry THF at −78° was added. The reaction mixture is stirred for 2 hours more and then quenched by adding 0.5 ml of acetic acid. The solvent was removed under reduced pressure and the residue extracted with methylene chloride and washed with water. After removal of solvent the residue was purified by chromatography on silica gel and eluted with 10% ether in methylene chloride to give the desired product.

EXAMPLE 2

1-benzyloxymethyl-5-ethyl-6-(α-pyridylseleno) uracil

In another embodiment, the synthesis of 1-benzyloxymethyl-5-ethyl-6-(α-pryidylseleno) uracil according to the present invention, can be prepared by the following synthesis route:

A solution of 3.2 g of metallic sodium in 100 ml of ethylene glycol monoethyl ether was chilled in an ice bath; hydrogen selenide, generated by the addition of dilute hydrochloric acid to aluminum selenide, was bubbled through the solution for 4 hr. To the dark red liquid 10 g of 2-bromopyridine was added. The mixture was refluxed for 19 hr., and the solids were removed by filtration. The filtrate was evaporated to dryness under reduced pressure at 70° C. The residue was dissolved in 80 ml of water and 20 ml of glacial acetic acid were added. The resultant red precipitate was filtered off with the aid of Celite and washed with water and methanol. The clear yellow filtrate was evaporated under reduced pressure until yellow needles began to form and then was cooled. The product was washed with cold water and dried over phosphorus pentoxide under vacuum. The product was recrystallized from benzene to give yellow needles.

To a solution of 1.58 g of 2-selenopyridine in 60 ml of water, 0.2 ml of 30% hydrogen peroxide was added with stirring. The product separated immediately as a yellow oil which solidified on standing. The diselenide was removed by filtration, washed with a small amount of water, and dried. The product was recrystallized from petroleum ether to yield yellow needles.

5-Ethyl-1-benzyloxymethyl uracil (520.5 mg, 2 moles) was dissolved in 10 ml of dry THF and cooled to −78° C. To the solution was added 3.6 ml of 1.4M LDA dropwise while stirring. After addition, the solution was stirred at −78° C. for 1 hour and 1.57 g (5 moles) of dipyridyl diselenide in 3 ml of dry THF at −78° C. was added. The reaction mixture was stirred for 2 hours more and then quenched by adding 0.5 ml of acetic acid. The solvent was removed under reduced pressure and the residue extracted with methylene chloride and washed with water. After removal of solvent the residue was purified by chromatography on silica gel and eluted with 10% ether in methylene chloride to give the desired product.

EXAMPLE 3

The procedure used to test the 6-pyridyl substituted pyrimidine derivatives activity against HIV is designed to detect agents acting at any stage of the virus reproductive cycle (see Weislow et al. (1989) *J. Nat'l. Cancer Inst.* 81:577–586, incorporated by reference herein). The assay basically involves the killing of T4 lymphocytes by HIV. Small amounts of HIV are added to cells, and a complete cycle of virus reproduction is necessary to obtain the required cell killing. Agents that interact with virions, cells, or virus gene-products to interfere with viral activities will protect cells from cytolysis. All tests are compared with at least one positive (e.g., AZT-treated) control done at the same time under identical conditions.

The procedure comprises:

1. The candidate pyrimidine derivative is dissolved in dimethyl sulfoxide then diluted 1:100 in cell culture medium before preparing serial half-$log_{10}$ dilutions. T4 lymphocytes (CEM cell line) are added and after a brief interval HIV-1 is added, resulting in a 1:200 final dilution of the compound. Uninfected cells with the compound serve as a toxicity control, and infected and uninfected cells with the compound serve as basic control.

2. Cultures are incubated at 37° in a 5% carbon dioxide atmosphere for 6 days.

3. The tetrazolium salt, XTT, is added to wells, and cultures are incubated to allow formazan color development by viable cells.

4. Individual wells are analyzed spectrophotomically to quantitate formazan production, and in addition are viewed microscopically for detection of viable cells and confirmation of protective activity.

5. Drug-treated virus-infected cells are compared with drug-tested noninfected cells and with other appropriate controls (untreated infected and untreated noninfected cells, drug containing wells without cells etc.) on the same plate.

6. Data are reviewed in comparison with other tests done at the same time and a determination about activity is made.

The anti-HIV activity profile of 1-benzyloxymethyl-5-ethyl-6-(α-pyridylthio) uracil determined by this procedure has been graphically represented in FIG. 1. A toxic concentration ($IC_{50}$) of $>9.8 \times 10^{-7}$ molar, an effective concentration ($EC_{50}$) of $9.00 \times 10^{-10}$ molar, and a therapeutic index ($TI_{50}$) of $>1.10 \times 10^{+3}$ molar was measured for this compound.

EXAMPLE 4

The 6-pyridylthio and 6-pyridylseleno pyrimidine derivatives of the present invention can be used to enhance the antineoplastic activity of anti-cancer therapeutics including 5-fluoropyrimidines (such as 5-FUra, 5-FdUrd, 5-Fluoro-1-(tetrahydro-2-furfuryl) uracil, etc.) against human cancer cell lines, as well as AZT-resistant sublines.

Preliminary in vitro cytotoxicity studies demonstrate that the combination of 5-fluorouracil (5-FUra) and 1-benzyloxymethyl-5-ethyl-6-(α-pyridylthio) uracil (BPTU) inhibits HCT-8 and HCT-8.clone 10 cell growth more effectively than 5-FUra alone.

In general, the experiments designed to assess the neoplastic activity of 5-fluoropyrimidines in conjunction with the 6-pyridyl substituted pyrimidine are carried out as follows.

Screw cap plastic tissue culture tubes are seeded with identical numbers of cultured tumor cells (approximately $2 \times 10^4$ cells/tube) in 4.8 mL RPMI-1640 containing 10% Fetal Bovine Serum (FBS) and 2% HEPES (IM buffer solution). The cultures are incubated overnight, on their sides, at 37° C. in a nonhumidified non-$C_2$ incubator.

The following day, the number of cells in duplicate tubes is determined. The media is decanted, the cells rinsed with Hanks' Balanced Salt Solution (calcium, magnesium and bicarbonate free) and replaced with 4.0 mL of trypsin-EDTA solution. The tubes are incubated at 37° C. for 5 minutes, then shaken to loosen the cells from the tube walls. To each tube is then added 1.0 mL of FBS and medium (50:50) in order to stop the action of the trypsin. Clumps of cells are broken apart by forceful repipetting with a 10 mL glass pipette. The resulting single cell suspension is counted using trypan blue exclusion and the total number of cells per tube recorded as the starting cell number.

Cells suspended in RPMI/FBS are preincubated with or without BPTU for 30 minutes, followed by addition of a given dose of 5-FUra. Tables 1 and 2 present the cell growth inhibition after 72 hours incubation with varying concentrations of 5-FUra, in the presence or absence of preincubation with 10 micromolar BPTU.

Table 1 demonstrates the increased efficacy of 5-FUra in conjunction with BPTU on cell growth in the HCT-8.clone 10 cell line (an AZT resistant clone). Similarly, Table 2 reports the effects of 5-FUra used in conjunction with BPTU on TM HCT-8 cells.

TABLE 1

Percent Growth Inhibition of HCT-8.clone 10 (AZT resistant) Cells

| 5-FUra (micromolar) | Without BPTU | With BPTU (10 micromolar) |
|---|---|---|
| 0 | 0 | 0 |
| 1 | 0 | 23 |
| 10 | 29 | 74 |
| 100 | 56 | >100 |

5-FUra alone at concentration of 10 micromolar had minimal inhibitory activity (29%). When BPTU (10 micromolar) was applied to the cells 30 minutes prior to 5-FUra, growth inhibition by 5-FUra (10 micromolar) was increased significantly to 74% (P<0.01).

TABLE 2

| 5-FUra (micromolar) | Percent Growth Inhibition HCT-8 Cells | |
|---|---|---|
| | Without BPTU | With BPTU (10 micromolar) |
| 0 | 0 | 0 |
| 1 | 0 | 33 |
| 3 | 9 | 55 |
| 10 | 33 | 80 |

This study shows that the combination of 5-FUra (10 micromolar) and BPTU (10 micromolar) inhibits HCT-8 cell growth more effectively than 5-FUra alone. 5-FUra alone had minimal activity (33% inhibition), while 30 minute incubation with 10 micromolar BPTU prior to addition of 10 micromolar 5-FUra resulted in an increase in inhibition to 80% (P<0.01).

Importantly, 1-benzyloxymethyl-5-ethyl-6-(α-pyridylthio) uracil alone at 10 micromolar was not shown to be growth inhibitory against either the human colon cancer HCT-8 or HCT-8.clone 10 cell lines.

What is claimed is:

1. A compound represented by the formula:

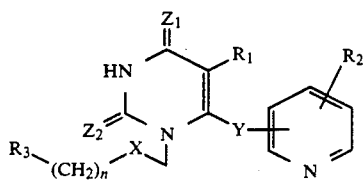

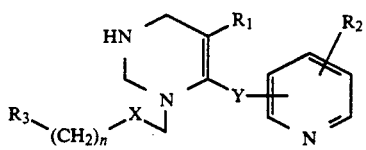

wherein $R_1$ is selected from the group consisting of a hydrogen, a halogen, an alkyl, an alkenyl, an alkynyl, a trifluoromethyl, a phenylthio, and a pyridylthio; $R_2$ is selected from the group consisting of a hydrogen, a halogen, an alkyl, an amino, a mono- or di-substituted amino, an azido alkyl, and an amino alkyl; $R_3$ is selected from the group consisting of a hydrogen, a halogen, an alkyl, an aryl, a substituted aryl, an azido alkyl, an amino alkyl, a trifluoromethyl, a pyridyl, and a quinolyl, provided $R_1$ and $R_2$ and $R_3$ as formulated do not interfere with the therapeutic utility of the compound; X is selected from a group consisting of sulfur and oxygen; Y is selected from a group consisting of sulfur and selenium; n is in the range of 0 to 5; and $Z_1$ and $Z_2$ are each selected from a group consisting of oxygen, sulphur and selenium.

2. A compound of claim 1 which is 1-benzyloxymethyl-5-ethyl-6-(α-pyridylthio) uracil.

3. A compound of claim 1 which is 1-benzyloxymethyl-5-ethyl-6-(α-pyridylseleno) uracil.

4. A pharmaceutical preparation comprising a 6-pyridyl substituted uracil derivative, or a pharmaceutically acceptable solvent thereof, in an amount effective to inhibit retroviral replication, the 6-pyridyl substituted uracil derivative represented by the formula:

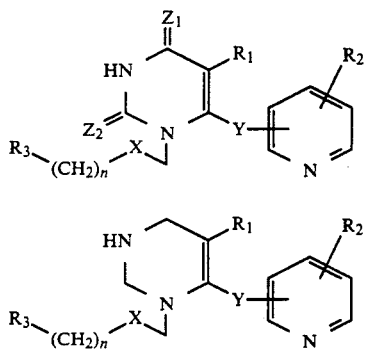

wherein $R_1$ is selected from the group consisting of a hydrogen, a halogen, an alkyl, an alkenyl, an alkynyl, a trifluoromethyl, a phenylthio, and a pyridylthio; $R_2$ is selected from the group consisting of a hydrogen, a halogen, an alkyl, an amino, a mono- or di-substituted amino, an azido alkyl, and an amino alkyl; $R_3$ is selected from the group consisting of a hydrogen, a halogen, an alkyl, an aryl, a substituted aryl, an azido alkyl, an amino alkyl, a trifluoromethyl, a pyridyl, and a quinolyl, provided $R_1$ and $R_2$ and $R_3$ as formulated do not interfere with the therapeutic utility of the compound; X is selected from a group consisting of sulfur and oxygen; Y is selected from a group consisting of sulfur and selenium; n is in the range of 0 to 5; and $Z_1$ and $Z_2$ are each selected from a group consisting of oxygen, sulphur and selenium.

5. The pharmaceutical preparation of claim 4 wherein the 6-pyridyl substituted uracil derivative is 1-benzyloxymethyl-5-ethyl-6-(α-pyridylthio) uracil.

6. The pharmaceutical preparation of claim 4 wherein the 6-pyridyl substituted uracil derivative is 1-benzyloxymethyl-5-ethyl-6-(α-pyridylseleno) uracil.

7. A method of inhibiting replication of a retrovirus, comprising contacting a retrovirally-infected cell with a 6-pyridyl substituted uracil derivative in an amount effective to inhibit viral replication in the infected cells, the uracil derivative represented by the formula:

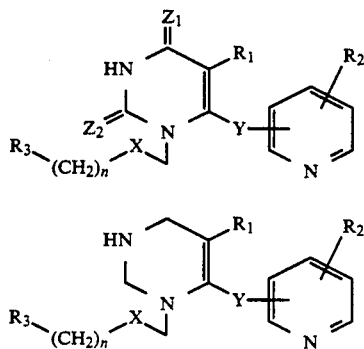

wherein $R_1$ is selected from the group consisting of a hydrogen, a halogen, an alkyl, an alkenyl, an alkynyl, a trifluoromethyl, a phenylthio, and a pyridylthio; $R_2$ is selected from the group consisting of a hydrogen, a halogen, an alkyl, an amino, a mono- or di-substituted amino, an azido alkyl, and an amino alkyl; $R_3$ is selected from the group consisting of a hydrogen, a halogen, an alkyl, an aryl, a substituted aryl, an azido alkyl, an amino alkyl, a trifluoromethyl, a pyridyl, and a quinolyl, provided $R_1$ and $R_2$ and $R_3$ as formulated do not interfere with the therapeutic utility of the compound; X is selected from a group consisting of sulfur and oxygen; Y is selected from a group consisting of sulfur and selenium; n is in the range of 0 to 5; and $Z_1$ and $Z_2$ are each selected from a group consisting of oxygen, sulphur and selenium.

8. The method of claim 7 wherein the uracil derivative is 1-benzyloxymethyl-5-ethyl-6-(α-pyridylthio) uracil.

9. The method of claim 7 wherein the uracil derivative is 1-benzyloxymethyl-5-ethyl-6-(α-pyridylseleno) uracil.

10. A method for improving the efficacy of a 5-fluoropyrimidine derivative in the treatment of cancerous cell growth in a subject comprising administering, in conjunction with an amount of the 5-fluoropyrimidine effective to inhibit growth of a cancerous cell, a compound represented by the formula:

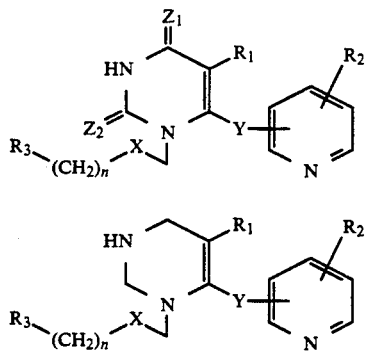

wherein $R_1$ is selected from the group consisting of a hydrogen, a halogen, an alkyl, an alkenyl, an alkynyl, a trifluoromethyl, a phenylthio, and a pyridylthio; $R_2$ is selected from the group consisting of a hydrogen, a halogen, an alkyl, an amino, a mono- or di-substituted amino, an azido alkyl, and an amino alkyl; $R_3$ is selected from the group consisting of a hydrogen, a halogen, an alkyl, an aryl, a substituted aryl, an azido alkyl, an amino alkyl, a trifluoromethyl, a pyridyl, and a quinolyl, provided $R_1$ and $R_2$ and $R_3$ as formulated do not interfere with the therapeutic utility of the compound; X is selected from a group consisting of sulfur and oxygen; Y is selected from a group consisting of sulfur and selenium; n is in the range of 0 to 5; and $Z_1$ and $Z_2$ are each selected from a group consisting of oxygen, sulphur and selenium.

11. The method of claim 10 wherein the 5-fluoropyrimidine is 5-fluorouracil.

12. The method of claim 10 wherein the compound administered in conjunction with the 5-fluoropyrimidine is 1-benzyloxymethyl-5-ethyl-6-(α-pyridylthio) uracil.

13. The method of claim 10 wherein the compound administered in conjunction with the 5-fluoropyrimidine is 1-benzyloxymethyl-5-ethyl-6-(α-pyridylseleno) uracil.

* * * * *